United States Patent
Yarmush et al.

(10) Patent No.: US 9,070,492 B2
(45) Date of Patent: Jun. 30, 2015

(54) NANOPOROUS METAL MULTIPLE ELECTRODE ARRAY AND METHOD OF MAKING SAME

(75) Inventors: Martin L. Yarmush, Newton, MA (US); Erkin Seker, Davis, CA (US); Yevgeny Berdichevsky, Bethlehem, PA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 12 days.

(21) Appl. No.: 13/822,747

(22) PCT Filed: Sep. 13, 2011

(86) PCT No.: PCT/US2011/051388
§ 371 (c)(1), (2), (4) Date: May 29, 2013

(87) PCT Pub. No.: WO2012/037118
PCT Pub. Date: Mar. 22, 2012

(65) Prior Publication Data
US 2013/0245416 A1 Sep. 19, 2013

Related U.S. Application Data

(60) Provisional application No. 61/382,610, filed on Sep. 14, 2010, provisional application No. 61/475,893, filed on Apr. 15, 2011.

(51) Int. Cl.
*A61B 5/0492* (2006.01)
*H01B 7/30* (2006.01)
(Continued)

(52) U.S. Cl.
CPC ................ *H01B 7/30* (2013.01); *A61B 5/0492* (2013.01); *A61B 5/04001* (2013.01); *G01N 33/4836* (2013.01)

(58) Field of Classification Search
CPC ........................ A61B 5/04001; A61B 5/0492
USPC .......................................... 600/373, 377, 378
See application file for complete search history.

(56) References Cited

U.S. PATENT DOCUMENTS 7,632,779 B1 12/2009 Ding et al.
2007/0123766 A1 5/2007 Whalen et al.
(Continued)

OTHER PUBLICATIONS

Erlebacher, et al., Evolution of Nanoporosity in Dealloying, Nature, 2001, 410:450-453.
(Continued)

*Primary Examiner* — Lee S Cohen
(74) *Attorney, Agent, or Firm* — Quarles & Brady, LLP

(57) ABSTRACT

A method is disclosed for fabricating a low-impedance nanoporous metal multiple electrode array for measuring electrophysiology activity. A patterned photoresist is applied to a substrate, in which the patterned photoresist corresponds to a pattern of the nanoporous metal multiple electrode array. A metal alloy including a sacrificial alloying element is deposited in the pattern of the nanoporous metal electrode array. The patterned photoresist is removed to expose the metal alloy as deposited. At least part of the sacrificial alloying element is removed from the metal alloy to create nanoporous metal electrode tips thereby forming the nanoporous metal multiple electrode array. The resultant nanoporous metal multiple electrode array has improved impedance characteristics in comparison to conventional multiple electrode arrays.

11 Claims, 8 Drawing Sheets

(51) Int. Cl.
*A61B 5/04* (2006.01)
*G01N 33/483* (2006.01)

(56) References Cited

U.S. PATENT DOCUMENTS

| | | |
|---|---|---|
| 2007/0293749 A1 | 12/2007 | Zhou et al. |
| 2009/0297913 A1 | 12/2009 | Zhang et al. |
| 2010/0210073 A1 | 8/2010 | Witvrouw et al. |
| 2010/0268055 A1* | 10/2010 | Jung et al. ............. 600/377 |
| 2011/0056398 A1 | 3/2011 | Weiss et al. |
| 2011/0208031 A1* | 8/2011 | Wolfe et al. ............. 600/378 |
| 2012/0091011 A1* | 4/2012 | Graham et al. ............. 205/775 |

OTHER PUBLICATIONS

Quan, et al., Development of Nanoporous Gold Electrodes for Electrochemical Applications, Microelectronic Engineering, 2011, 88(8):2379-2382.

Seker, et al., The Fabrication of Low-Impedance Nanoporous Gold Multiple-Electrode Arrays for Neural Electrophysiology Studies, Nanotechnology, 2010, 21(12):125504, 13 pages.

Zhou, et al., Integration of Au Nanorods with Flexible Thin-Film Microelectrode Arrays for Improved Neural Interfaces, Journal of Microelectromechanical Systems, 2009, 18(1):88-96.

The International Search Report and Written Opinion as mailed on Apr. 9, 2012 for International Application No. PCT/US2011/051388.

* cited by examiner (a)

(b)

(c)

NANOPOROUS METAL MULTIPLE ELECTRODE ARRAY AND METHOD OF MAKING SAME

CROSS-REFERENCE TO RELATED APPLICATION

This patent application represents the national stage entry of PCT international application no. PCT/US2011/051388 filed on Sep. 13, 2011 which claims priority to U.S. provisional patent application Ser. No. 61/382,610 entitled "Nanoporous Metal Multiple Electrode Array and Method of Making Same" filed on Sep. 14, 2010 and to U.S. provisional patent application Ser. No. 61/475,893 entitled "Neural Electrode Array and Methods of Using Same" filed on Apr. 15, 2011. The full contents of those applications are incorporated by reference as if set forth in their entirety herein.

STATEMENT REGARDING FEDERALLY SPONSORED RESEARCH

This invention was made with the government support under P41-EB002503 and F32-MH079662 awarded by the National Institutes of Health and DMI-0507023 awarded by the National Science Foundation. The government has certain rights in the invention.

BACKGROUND OF THE INVENTION

This invention relates to multiple electrode arrays for measuring electrophysiological activity and the fabrication of multiple electrode arrays of this type.

Planar multiple electrode arrays (MEAs) have become a widely used tool in neuroscience. Planar MEAs are typically employed in vitro to detect, in parallel, field potentials or unit activity from many locations in brain slices or cultures. Some of the most promising applications of MEA technology involve long-term activity recording from cell or slice cultures (see e.g., Gross et al., 1982, Recording of spontaneous activity with photoetched microelectrode surfaces from mouse spinal neurons in culture, *J Neurosci Methods* 5 13-22; Pancrazio et al., 2003, A portable microelectrode array recording system incorporating cultured neuronal networks for neurotoxin detection, *Biosens Bioelectron* 18 1339-47; Eytan et al., 2003, Selective adaptation in networks of cortical neurons, *J Neurosci* 23 9349-56; Morin et al., 2006, Constraining the connectivity of neuronal networks cultured on microelectrode arrays with microfluidic techniques: a step towards neuron-based functional chips, *Biosens Bioelectron* 21 1093-100; Chang et al., 2001, Modulation of neural network activity by patterning, *Biosens Bioelectron* 16 527-33; Nam et al., 2004, Patterning to enhance activity of cultured neuronal networks, *IEEE Proc Nanobiotechnol* 151 109-15; Uesaka et al., 2007, Interplay between laminar specificity and activity-dependent mechanisms of thalamocortical axon branching, *J Neurosci* 27 5215-23).

As the size of MEAs decrease, obtaining readings from MEAs with a high signal-to-noise ratio has proven to be increasingly difficult. On one hand, there is a drive to decrease the size of the electrodes to increase the spatial resolution of the MEAs. Unfortunately, as the diameter, size, and/or footprint of electrodes decrease, the impedance of the electrodes increases, which decreases the quality or sensitivity of the readings.

To attempt to minimize the impedance in the electrodes as they are reduced in size, many have added surface coatings to the tips of the electrodes. Design of these surface coatings has been a challenge as, in addition to lowering electrode impedance, these coatings should be stable in aqueous solutions and capable of being fabricated at low cost.

To date, the most commonly used coating is electrochemically deposited platinum black (see e.g., Jones et al., 1935, The measurement of the conductance of electrolytes. VII. On platinization. *Journal of the American Chemical Society* 57 280-4; Geddes, 1972, Electrodes and the Measurement of Bioelectric Events). While platinum black improves electrode impedance, it has the drawbacks of poor deposition reproducibility and durability. Some alternatives to platinum black include the use of ceramic materials as surface coatings such as porous titanium nitride (Bauerdick et al., 2003, BioMEMS Materials and Fabrication Technology, *Biomedical Microdevices* 5 93-9), porous silicon (Moxon et al., 2004, Nanostructured surface modification of ceramic-based microelectrodes to enhance biocompatibility for a direct brain-machine interface, *IEEE Trans Biomed Eng* 51 881-9), or conductive polymers (Cui X et al., 2001, Electrochemical deposition and characterization of conducting polymer polypyrrole/PSS on multichannel neural probes, *Sensors and Actuators A* 93 8-18; Yang and Martin, 2004, Microporous conducting polymers on neural microelectrode arrays II. Physical characterization, *Sensors and Actuators A-Physical* 113 204-11).

These materials, when used to fabricate the electrodes or to form a surface coating, lower electrode impedance. However, they frequently require sophisticated processing equipment leading to high chip costs, and sometimes suffer from poor reproducibility, process integration issues, and delamination (Cui and Martin, 2003, Fuzzy gold electrodes for lowering impedance and improving adhesion with electrodeposited conducting polymer films, *Sensors and Actuators A-Physical* 103 384-94).

In addition, current implantable neural interfaces have poor long-term stability. The underlying cause of this instability is not fully understood and is likely a combination of multiple factors, including local and systemic physiological responses to indwelling electrodes and failure attributed to device malfunction. In any event, neural interfaces typically have difficulty accurately detecting activity of the neural tissue as over time glial scaring can form at the attachment site of the electrodes and the electrodes may otherwise separate from the functional tissue. Several approaches, including integrated microfluidic channels for drug delivery and drug-eluting polymers, have been explored to suppress glial scar formation. However, due to the constraints with electrode footprint and impracticalities associated with microfabrication, most of these approaches are ineffective.

Hence, a need exists for an improved multiple electrode array that reduces impedance at the electrode tips while remaining functionally viable in a neural environment.

SUMMARY OF THE INVENTION

Although low electrode impedance is a figure of merit for sensitive detection of neural electrical activity and numerous studies have aimed to reduce impedance, fabrication of a robust multiple electrode array that significantly reduces impedance while obtaining high spatial resolution has proven to be a challenge. Unfortunately, to date, most efforts to do so have been tethered by a combination of poor functional coating adhesion, complicated fabrication techniques, and poor fabrication repeatability.

A nanoporous metal multiple electrode array and related method of fabricating the same is disclosed as a new approach to address these issues.

The disclosed nanoporous metal MEA and related method of making has many benefits. The method utilizes simple microfabrication techniques in a unique way to create a novel structure having much sought after, but previously unachieved, impedance and spatial resolution qualities. The resultant multiple electrode arrays exhibit lower impedance than the present state-of-the-art platinum black electrodes.

Moreover, these MEAs may be configured to support and controllably release a chemical agent (e.g., a pharmaceutical). In some instances, this chemical agent may be used to improve the biocompatibility of the MEA and permit high-fidelity long term recordings. In other instances, the MEA may monitor neural activity and the MEA may be configured to controllably release the chemical agent for therapeutic or diagnostic purposes.

In one preferred form of the device, the electrode tips include a gold material so that a nanoporous gold multiple electrode array is formed (which may be referred to as a "np-Au MEA"). The np-Au MEA has a thiol-based gold surface chemistry that may further allow advanced functionalization of the electrodes (e.g., immobilization of extra-cellular matrix proteins). Moreover, the high surface area-to-volume ratio of self-assembled nanoporous gold can result in more than a 25-fold improvement in electrode-electrolyte impedance, where at 1 kHz, 850 kΩ impedance for conventional Au electrodes is reduced to 30 kΩ for np-Au electrodes. Low impedance provides superior signal-to-noise ratio for detection of neural activity in noisy environments. The fabricated np-Au MEAs may be used to measure electrophysiological activity in vitro or in vivo.

The electrophysiological tools described herein may be applicable to the study of numerous neurological disorders including, but not limited to, epilepsy, traumatic brain injury, Parkinson's disease, Alzheimer's disease, Huntington's disease, amyotrophic lateral sclerosis (ALS), and sight- and hearing-loss. Moreover, these tools may also be used to administer therapeutic treatments.

These and still other advantages of the invention will be apparent from the detailed description and drawings. What follows is merely a description of some preferred embodiments of the present invention. To assess the full scope of the invention, the claims should be looked to as these preferred embodiments are not intended to be the only embodiments within the scope of the claims.

BRIEF DESCRIPTION OF THE DRAWINGS

FIG. 3a illustrates that there is more than a 25-fold magnitude improvement in impedance for np-Au electrodes compared to conventional compact gold electrodes. FIG. 2b shows that the impedance, Z, of nanoporous gold MEAs generally decrease with increasing thickness, as total surface area scales with thickness, as indicated by the arrow. FIG. 3c illustrates that the electrode impedance at 1 kHz is inversely proportional to total surface area of the electrode.

DETAILED DESCRIPTION OF THE PREFERRED EMBODIMENTS

Figure 1:
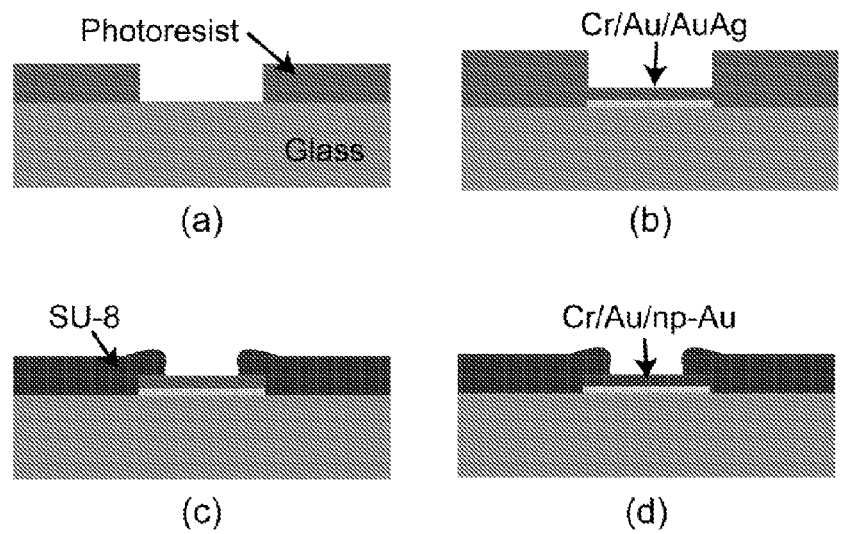
FIG. 1 illustrates the various steps of the fabrication of a np-Au multiple electrode array including: (a) patterning a 4 μm-thick photoresist on a glass microscope slide; (b) sputter-depositing adhesion promoting layers and a gold-silver alloy composition; (c) after removing the photoresist from the electrodes, patterning a 2 μm-thick SU-8 layer to insulate the electrodes except for the approximately 32 μm-diameter circular sensing regions and peripheral electrical contacts; (d) dealloying the electrodes in nitric acid at 70° C. to produce nanoporous gold electrodes.

A method is disclosed for fabricating a low-impedance nanoporous metal multiple electrode array for measuring electrophysiology activity. A patterned photoresist is applied to a substrate, in which the patterned photoresist corresponds to a pattern of the nanoporous metal multiple electrode array. A metal alloy including at least one sacrificial alloying element is deposited in the pattern of the nanoporous metal electrode array. The patterned photoresist is removed to expose the metal alloy as deposited. At least part of the sacrificial alloying element is removed from the metal alloy to create a plurality of nanoporous metal electrode tips thereby forming the nanoporous metal multiple electrode array.

A patterned insulation layer may be applied on the as-deposited metal alloy between the step of removing the patterned photoresist and removing at least part of the sacrificial alloying element. The patterned insulation layer may substantially cover the metal alloy as deposited, but does not cover the electrode tips and the peripheral electrode contact pads such that they remain exposed. The step of removing at least part of the sacrificial alloying element may include removing the sacrificial alloying element in the plurality of electrode tips to create the plurality of nanoporous metal electrode tips. The contact pads on the periphery of the glass chip substrate may also remain exposed and become nanoporous after removal of the sacrificial alloying element by, for example, dealloying.

The metal alloy may include gold and silver and the sacrificial alloying element may be silver. In this case, the step of removing at least part of the sacrificial alloying element from the metal alloy may include exposing the gold alloy to nitric acid to thereby remove the silver from the gold alloy. An impedance of the nanoporous gold multiple electrode array of this type may be at least twenty-five times less than an impedance of a multiple electrode array of similar dimensions of gold that is substantially pore-less.

In any event, the metal alloy may be a multi-constituent system in which at least one of the constituents can be chemically removed by dealloying the less noble constituent of the alloy or the like such that the remaining constituent (e.g., the gold in the gold-silver alloy system) self assembles into a porous structure. Although a gold-silver system is described in the example below, other alloy systems may also be used including, but not limited to, gold-aluminum and gold-silver-platinum, and platinum-silicon. Additionally or alternatively, porous electrodes might be fabricated using metals that are commonly used for electrodes such as, for example, platinum, tungsten, and iridium.

At least one adhesion-promoting layer may be applied to the substrate before deposition of the metal alloy. This adhesion promoting layer may include the deposition of a chrome layer onto the substrate followed by a deposition of a gold layer onto the chrome layer. The substrate could be any of a number of materials including, for example, a glass microscope slide, a silicon wafer, or other inorganic substrates.

In some forms, the deposition of the metal alloy may be performed by a sputter coating process. The type of deposition and the amounts of the constituents of the metal alloy may be altered to create different initial metal alloy morphologies and, accordingly, nanoporous metal electrode types having varied properties based on the resultant tip structure after removal of the sacrificial alloying element.

The nanoporous metal multiple electrode array may have a percent porosity of between approximately 26% and approximately 38%. It will be appreciated, however, that the pore morphology (i.e., porosity, pore size, and matrix structure) can be controlled by varying initial alloy constituents, varying dealloying conditions, and/or post-synthesis thermal or chemical treatment.

A nanoporous metal multiple electrode array is also disclosed as made by the methods described above.

In one form, the MEA is a low-impedance nanoporous metal multiple electrode array for measuring electrophysiology activity. The array includes a patterned multiple electrode array made of a metal alloy. The patterned multiple electrode array has a plurality of leads each extending from a contact pad to a nanoporous metal electrode tip. The nanoporous metal electrode tip is configured to measure electrophysiological activity.

The nanoporous metal electrode tip is configured to reduce the impedance of the electrode tip relative to a substantially pore-less metal electrode tip of similar dimensions. The impedance of a nanoporous gold electrode tip may be at least approximately twenty five times less than the impedance of the substantially pore-less gold electrode tip of similar dimensions. The nanoporous metal multiple electrode array may have a percent porosity of between approximately 26% and approximately 38%.

The electrode tips may substantially comprise a nanoporous metal material and at least a portion of the lead may comprise a metal alloy including a sacrificial alloying element. In some forms, the sacrificial alloying element may be silver and the remaining element that forms the nanoporous structure may be gold.

To electrically isolate the leads from one another, the leads may be substantially covered by a patterned insulation layer except for the electrode tips and the contact pads.

It is contemplated that a nanoporous metal material of the type described above may be used not only to lower impedance and improve the signal-to-noise ratio of the electrode leads, but may also be modified to alleviate adverse tissue response, thereby permitting long-term high fidelity recordings, and/or monitor and modulate physiological activity. The nanoporous material may be engineered to serve as a type of nanoporous "sponge" that holds and releases chemical agents to achieve these ends.

By controllably releasing pharmaceuticals (such as, for example, anti-inflammatories and immunosuppressants), glial scarring may be to suppressed or blunted and the electrode may sustain low electrode impedance thereby enabling high-fidelity long-term recordings. The high specific surface area of nanoporous materials enables prolonged release of small molecules, as nanofluidic mechanism dominate over simple Fickian diffusive mechanisms, which should allow in situ management of the foreign body response.

Moreover, in some forms, the nanoporous metal material may be configured to selectively administer therapeutic agents. Thus may be helpful for the treatment of, for example, epileptic seizures.

Accordingly, the nanoporous electrode materials can serve the multiple purposes of exhibiting high specific surface area for low impedance and also retaining/supporting small molecules (such as drugs or pharmaceuticals) within its porous network for improved biocompatibility and selective release.

A specific example of the process or method used to form a nanoporous gold multiple electrode array is provided below followed by examples how to fabricate drug-elucidating neural devices to mitigate adverse tissue response, create neural electrodes that enable long-term high sensitivity recordings in vivo, and monitor and modulate pathological neural activity triggered by drug delivery. These examples are offered for illustrative purposes only, and are not intended to limit the scope of the present invention in any way. Indeed, various modifications of the invention in addition to those shown and described herein will become apparent to those skilled in the art from the foregoing description and the following example and fall within the scope of the appended claims.

EXAMPLE I

Various materials used in preparation of the nanoporous gold multiple electrode arrays were obtained as follows. Glass slides 75 mm×50 mm were purchased from VWR (West Chester, Pa.). Gold, silver, and chrome targets were all 99.95% pure and obtained from Kurt J. Lesker (Clairton, Pa.). Ethanol, methanol, acetone, sulfuric acid, hydrogen peroxide, hexamethyldisilazane (photoresist adhesion promoter) were obtained from Sigma-Aldrich (St. Louis, Mo.). AZ400K developer and AZ4330 positive photoresist (PR) were obtained from Clariant Corporation (Somerville, N.J.). SU8-2 and Edge Bead Removal solution (SU8 developer) were obtained from Microchem Corporation (Newton, Mass.). Polydimethylsiloxane (PDMS) kit was obtained from Sylgard 184, Dow Corning (Wilmington, Mass.). Silicon wafers were obtained from Silicon Quest International, Inc. (Santa Clara, Calif.). Impedance measurements and field potential recordings were carried out in artificial cerebrospinal fluid (ACSF), composed of 120 mM NaCl, 3.3 mM KCl, 1.25 mM $NaH_2PO_4$, 26 mM $NaHCO_3$, 1.3 mM $CaCl_2$, 0.9 mM $MgCl_2$, and 10 mM glucose in deionized water.

Referring now to FIG. 1, the key steps of the fabrication process for producing nanoporous gold multiple electrode array are schematically outlined.

First, the glass slide substrates were immersed in "piranha" solution consisting of 1:3 ratio of hydrogen peroxide (30% w/v) and sulfuric acid (50% v/v) for 15 minutes, rinsed in running deionized (DI) water, and dried under nitrogen. The cleaned glass slides were spin-coated with 4 µm-thick positive photoresist, which was photolithographically patterned as generally indicated in FIG. 1a. The lithography masks were drawn with AutoCAD and printed on transparencies at Fineline Imaging (Colorado Spring, Colo.).

The patterned photoresist layer functioned as a stencil mask for electrode deposition, for which a Kurt J. Lesker direct-current magneto-sputtering instrument was employed. Each sample was initially coated with 20 nm-thick chrome layer and 120 nm-thick gold layer to promote adhesion of the gold alloy coating. Following the deposition of the chrome and gold layers, the gold target gun power was kept at 100 W and the silver target gun power was kept at 200 W to deposit the gold alloy. All depositions were performed under 10 mTorr of Argon. Different film thicknesses were obtained by varying the deposition time and different alloy compositions by varying the silver target gun power. In some forms, the deposited gold alloy is less than 1 µm-thick. After the chrome, gold, and gold alloy layers were deposited, the samples had the form illustrated in FIG. 1b.

Following film deposition, the samples were sonicated in acetone and methanol successively to remove the photoresist layer and to reveal electrode patterns on glass. Then, a 2 µm-thick SU-8 electrical-insulation layer was photolithographically patterned on the multiple electrode array, exposing only the 32 µm-diameter electrode tips and peripheral electrode contact pads. This structure is shown in FIG. 1c at a cross-section taken through an exposed electrode tip in the MEA.

After measuring electrode thickness, we produced the nanoporous gold structure at the electrode tips by immersing the samples in nitric acid (65%) at 70° C. for 5 minutes until electrode color no longer changed. The resultant structure having the np-Au electrode tips is illustrated in FIG. 1d. The compact-gold control electrodes were fabricated similarly, except that no silver co-deposition or dealloying was performed.

Immersion of the gold-silver alloy in nitric acid results in surface diffusion of gold and silver atoms, and selective dissolution of silver atoms, which produces a structure with open-pore morphology (see Erlebacher et al., cited above). The main advantage of this technique is its reproducibility and compatibility with conventional microfabrication techniques, thus enabling its scalability and broadening its applications in microsystems. Elemental analysis of the dealloyed materials indicated less than 5 atomic percent residual silver in the films. During dealloying, some amount of silver is passivated by surrounding gold atoms and is not attacked by acid.

Figure 2:
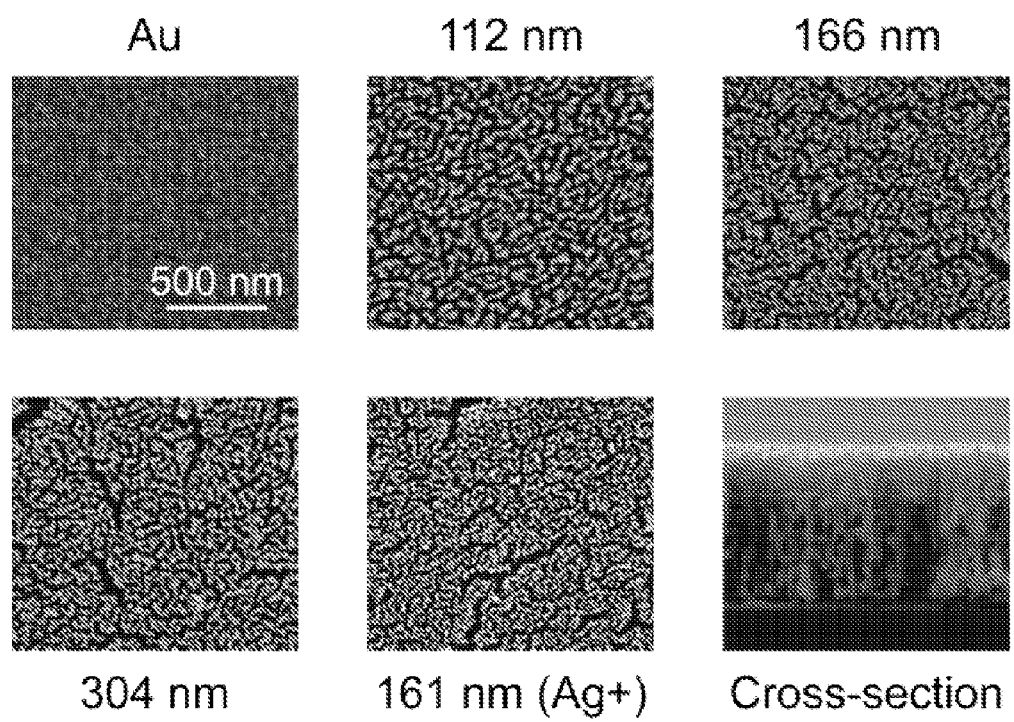
FIG. 2 is a number of scanning electron microscope images of MEAs having different film thickness at the same magnification. "Ag+" indicates the sample that had a higher initial silver concentration. The bottom right SEM image includes a cross-sectional image illustrating the homogenous pore morphology along the film thickness (a thicker film is intentionally presented to demonstrate consistent homogeneity across a large thickness).

FIG. 2 show high-magnification scanning electron micrographs of the different MEAs produced which were used in performing the tests that will be described in further detail below. The compact-gold control electrode displayed typical granularity of a sputtered film while the porous electrodes exhibited micro-scale voids due to volume shrinkage during dealloying. These voids do not necessarily affect electrode performance, but actually improve film adhesion by mitigating tensile stress accumulation that usually leads to film delamination.

We used ImageJ (NIH shareware available from http://rsb.info.nih.gov/ij/index.html) for np-Au porosity analysis, as described elsewhere (Seker et al., 2007, The effects of post-fabrication annealing on the mechanical properties of freestanding nanoporous gold structures, Acta Mater. 55 4593-602). First, the gray-scale images were manually segmented into monochrome images by selecting a threshold gray value that separated dark pores and light ligaments. We used the built-in "watershed" tool to separate the segmented pores into approximately circular individual pieces. The percent area covered by the pores and the area of each circular piece were calculated with the built-in "particle analysis" algorithm in ImageJ.

We then approximated the total surface area of an electrode as follows. The total volume of the spherical pores within a single circular electrode tip is:

$$V_{pores} = \beta h \pi R^2$$

where $\beta$ is the porosity, h is the film thickness, and R is the radius of the electrode tip. The number of spherical pores that can fill the volume total volume is:

$$N_{pores} = \frac{V_{pores}}{V_{one\_pore}} = \frac{3\beta hR^2}{4r^3}$$

where r is the spherical pore radius, which was calculated from pore area that corresponded to one standard deviation above the mean pore area for normally-distributed pore areas. We then used the number of pores to compute the total surface area:

$$A_{surface} = N_{pores} \cdot 4\pi r^2 = \left(\frac{\beta h}{r}\right) \cdot 3\pi R^2$$

We analyzed the micrographs with ImageJ digital imaging software to obtain percent porosities (ratio of dark area to total image area) and areas of individual pores. 2D porosity of the surface is consistent through the film thickness, as the homogenous pore morphology in the SEM cross-section suggests as illustrated in FIG. 2. We therefore concluded that porosity and area data obtained by analysis of the 2D image can be used to make an estimate of the total surface area. Percent porosities of the films were 38%, 32%, and 34% for increasing film thickness (standard alloy composition) and 26% (higher initial silver content, denoted as "Ag+" in FIG. 2). The mean pore radii were 20 nm, 41 nm, and 31 nm for increasing film thickness (standard alloy composition) and 22 nm (Ag+). Nanoporous gold film thicknesses were 112 nm, 166 nm, and 304 nm (standard alloy composition) and 161 nm (Ag+). The total surface area generally increased with film thickness. Despite the moderate thickness and lower percent porosity of the "Ag+" film, its total surface area was comparable to the thickest np-Au film. As seen in equations above, the total surface area scales with (βh/r); that is, the initial silver-rich alloy resulted in smaller pore sizes, which in turn yielded a high total surface area.

In some forms, the gold atoms may be self-assembled into a porous sponge having an average pore size of 50 nm and an average porosity of 35%. This amount of surface roughness has been shown to promote neural attachment to the electrodes. However, it will be appreciated that the pore morphology may be tuned using, for example, thermal treatment and may be modified to increase electrode sensitivity for a particular application, environment, and/or electrode material composition.

Before taking any impedance measurements or taking recordings from brain slices, the samples were thoroughly washed in deionized water, soaked in deionized water at least overnight, and dried under nitrogen. Ideally, impedance measurements should be taken when electrodes are fresh, since prolonged exposure of electrodes to air reduces their wetting ability; however, this can be remedied by a short oxygen plasma cleaning, as described elsewhere (see e.g., Seker et al., 2008, Kinetics of capillary wetting in nanoporous films in the presence of surface evaporation, *Appl. Phys. Lett.* 92 0131-28).

We measured the impedance of the prepared np-Au MEAs and control MEAs by applying a 200 mV amplitude signal between MEA electrodes and an Ag/AgCl counter electrode, in ACSF, at frequencies ranging between 0.5 kHz and 20 kHz. We measured a minimum of five electrodes for each type of np-Au MEAs and for regular compact-Au MEA. To measure impedance as a function of electrode area, we prepared np-Au MEAs without SU-8 insulation. We then cut an opening in a 50 μm-thick PDMS film, and aligned the film to the MEA such that a portion of the electrode tip, or the electrode tip as well as a portion of its connecting trace, was exposed to ACSF. We determined the exposed area of np-Au with ImageJ analysis of digital micrographs of the electrodes.

Figure 3:
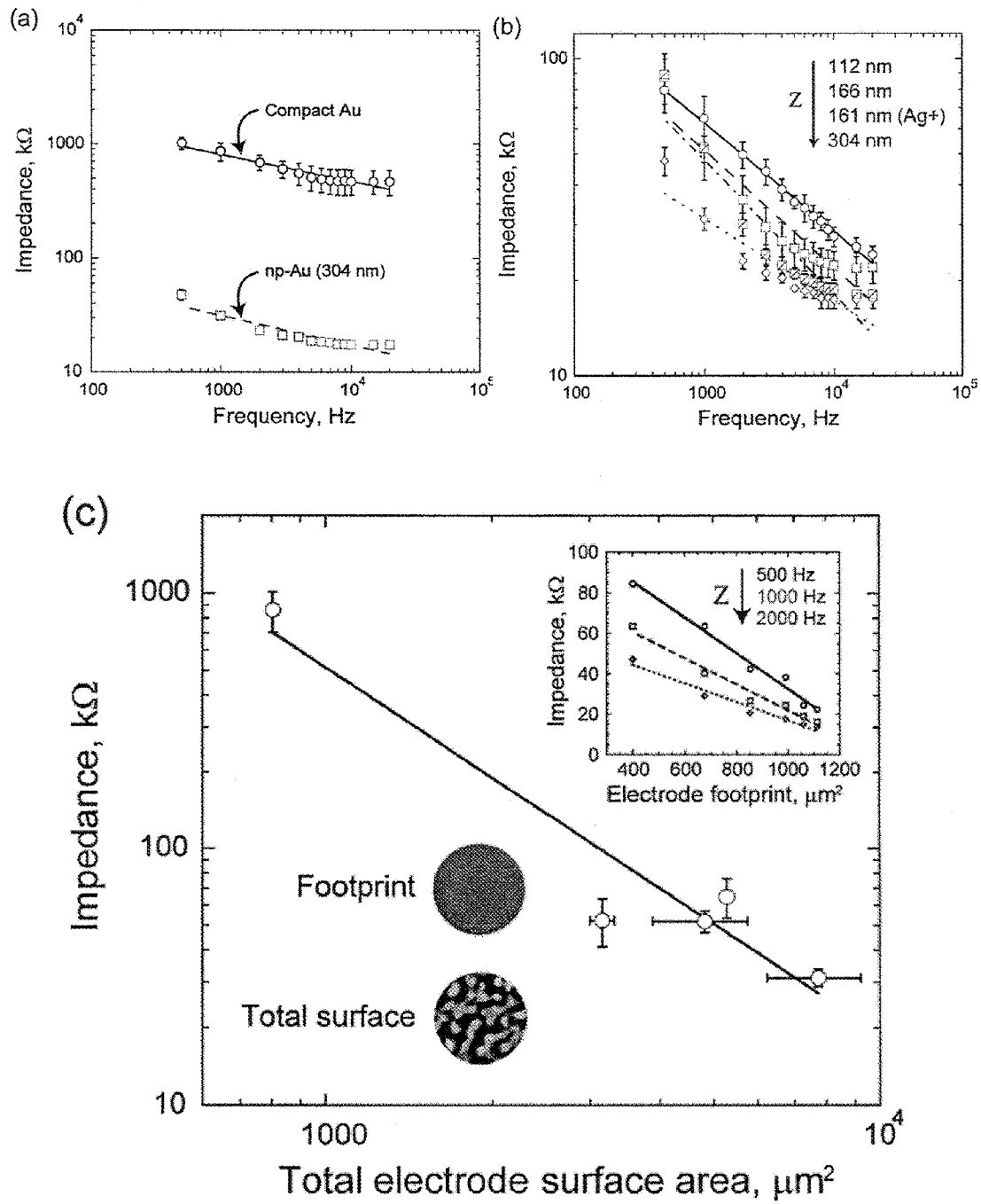
FIG. 3 shows impedance for MEAs with different film thicknesses and initial alloy composition.

FIG. 3a illustrates the greater than 25-fold decrease in impedance of the np-Au electrode (304 nm thick) compared to the gold control electrode, as a result of augmented total surface area. This 304 nm-thick electrode yields an impedance of approximately 30 kΩ at 1 kHz, which is also notably three times lower than the typical 100 kΩ impedance of conventional platinum black electrodes at this frequency (as indicated in Robinson, 1968, The electrical properties of metal microelectrodes, Proceedings of the IEEE 56 1065-71). Platinum black electrodes are traditionally produced by platinum electroplating of a rough platinum layer, thereby enhancing the effective electrode surface area. Unfortunately, electroplating requires additional fabrication steps and suffers from process-to-process and across-substrate variations.

FIG. 3b provides a comparison of np-Au electrodes with varying thicknesses and initial alloy composition. The electrode impedance generally decreased with increased film thickness for electrodes with the same initial alloy composition, as expected from the relationship, $$1/Z \propto A_{surface} \propto (\beta h/r)$$

where Z is the electrode impedance. However, as the np-Au film produced by dealloying a silver-rich alloy (Ag+) leads to total surface area comparable to that of the 304 nm-thick np-Au electrode, the impedance for the Ag+ electrode is also comparable to that of the 304 nm-thick np-Au electrode. As the MEA with a higher pre-dealloying silver content created a structure with higher unit surface area per thickness, this sample had less impedance compared to MEAs with less silver content of a similar thickness.

Error bars in FIG. 3b display the standard deviation of measurements from at least five different electrodes on a chip and suggest a high electrode-to-electrode repeatability attained by the developed fabrication method. In addition, consistently lower impedance values across different np-Au electrode types evidence the repeatability of the overall impedance improvement.

FIG. 3c demonstrates the relationship between impedance and total electrode surface area at 1 kHz. We fabricated a np-Au chip (identical to the 304 nm-thick MEA that displayed the biggest impedance enhancement) without the SU-8 insulation layer in order to systematically vary the electrode area exposed to electrolyte to determine the impedance-area relationship. Our aim was to study the linearity of impedance versus electrode-footprint relationship. Horizontal error bars indicate standard deviations of total surface area, which were calculated using three different scanning electron micrographs and film thickness measurements per sample.

The inset of FIG. 3c illustrates the relationship between impedance and the electrode footprint. As seen in the inset, the impedance decreased linearly between an electrode footprint of 400 μm² to 1100 μm². As indicated by the arrow, with increasing excitation frequency, measured impedance decreases for a given electrode footprint area.

To test the fabricated np-Au MEAs, we prepared hippocampal slices and then recorded spontaneous activity in the prepared hippocampal cultures.

First, we dissected 350 μm-thick hippocampus slices from postnatal day 7 Sprague-Dawley rat pups (Charles River Laboratories) and maintained them as interface-type organotypic cultures in a humidified 5% $CO_2$ incubator at 37° C. Organotypic brain slices are effective tools for studying physiological and pharmacological properties of neuronal networks, as they preserve the cytoarchitecture of the brain. We used serum-containing (1:1:2 horse serum, Hanks' Balanced Salt Solution, and Basal Medium Eagle, supplemented with 1 mM glutamine and 30 μg/ml gentamicin, all from Invitrogen) for first 24 hours of culture, and then substituted it with serum-free medium (Neurobasal A/B27, with 0.5 mM glutamine and 30 μg/ml gentamicin, all from Invitrogen), which was then used in all subsequent medium changes (every 3 days). The experiments were conducted with the guideline and approval of the Massachusetts General Hospital Subcommittee on Research Animal Care.

In order to record field potentials using the np-Au MEA, we used the method recently developed by our group (described in Berdichevsky et al., 2009, Microfluidics and multielectrode array-compatible organotypic slice culture method, *Journal of Neuroscience Methods,* 178 59-64). Briefly, we fabricated a flexible 150 μm-thick PDMS film with a 3 mm-diameter well to accommodate hippocampus slice cultures. We then placed the film onto a np-Au MEA so that the slice well was centered on the electrode array. We gently removed organotypic slices from culture dishes on 21st day in vitro (DIV), and placed them into the PDMS well on np-Au MEA. We acquired recordings from the hippocampal cultures in ACSF (composition described above) and ACSF with 2.1 mM KCl addition in a humidified 5% $CO_2$, 37° C. incubator. Signals from MEA were amplified, digitized, and filtered with 3 Hz high-pass filter and 55-65 Hz band-stop Butterworth filter (to remove line noise).

Figure 4:
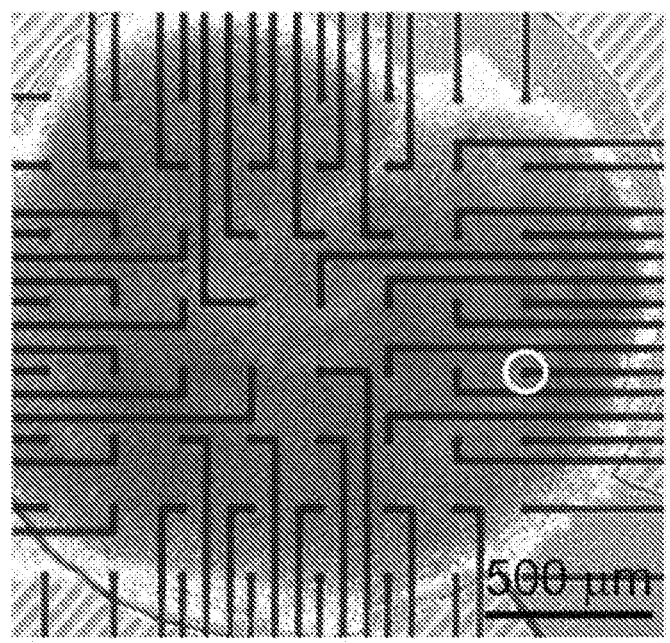
FIG. 4 provides (a) a micrograph of hippocampal brain slice over a np-Au MEA in which the circle indicates the electrode position in the CA3 region where the field potentials were recorded; (b) recordings of multi-unit spontaneous activity of slice in physiological buffer; and (c) recordings of epileptiform bursts induced by elevated [$K^+$].
Figure 4:
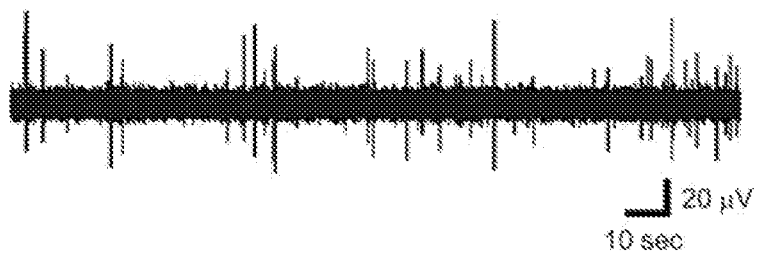
Figure 4:
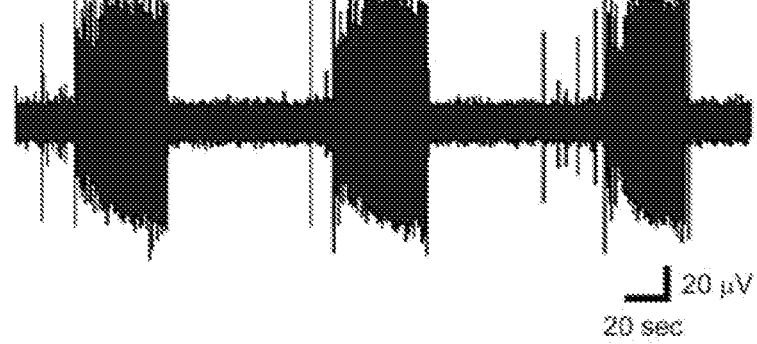

As illustrated in FIG. 4a, we placed a 21 DIV organotypic hippocampal slice culture onto a np-Au MEA and recorded spontaneous activity. Multiple unit spontaneous activity was observed in ACSF as shown in FIG. 4b, and epileptiform bursts were recorded in ACSF containing an elevated concentration of $K^+$ (5.4 mM) as shown in FIG. 4c.

Unit activity in slices is generally hard to detect with planar MEA electrodes. This is due to low amplitude of single units (<100 µV) and the physical separation between planar electrodes and the axon initial segment (the region that is thought to be responsible for most of the extracellular signal generated by an action potential). The physical separation is caused by surface layers of dead cells in acute slices or by a surface layer of glia in organotypic cultures.

Figure 5:
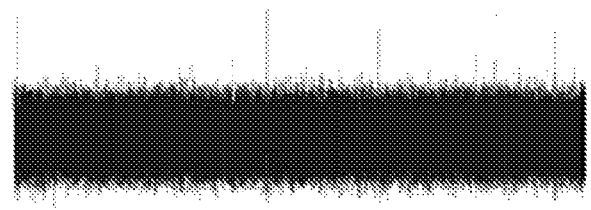
FIG. 5 shows recordings of multi-unit spontaneous activity from a CA3 region of a slice that illustrates that np-Au electrodes provide much higher signal-to-noise ratio when compared to standard gold electrodes.
Figure 5:
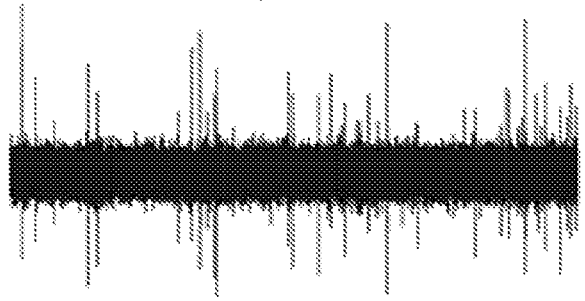

However, as illustrated by the comparison recordings of multi-unit spontaneous activity from CA3 region using np-Au MEAs and standard gold electrodes in FIG. 5, the np-Au electrodes have a much higher signal-to-noise ratio in comparison to standard gold electrodes. Low impedance of np-Au electrodes helped reduced noise levels (random noise at the electrode-electrolyte interface as well as contributions from the noisy environment of the incubator where recordings were performed and the length of electrical lines between the incubator and amplifiers) to the point where unit activity could be detected. On the other hand, the standard electrodes were significantly noisier, and lower amplitude single units (from neurons located further away from the recording electrode) could not be discerned.

This experiment demonstrated the utility of np-Au MEA electrodes in recording neural activity ranging from single units to network-wide bursts with high sensitivity.

The fabricated nanoporous gold material exhibited excellent lamination properties. The nanoporous gold films remained intact throughout our experiments and prolonged immersion (greater than 4 months) in phosphate buffered saline solution, whereas most polymers swell in the presence of liquid and delaminate due to mechanical instability (Green et al., 2008, Conducting polymers for neural interfaces: challenges in developing an effective long-term implant, Biomaterials 29 3393-9).

In sum, a simple, scalable, and repeatable technique to produce multiple electrode arrays with impedance values better than those of state-of-the-art platinum black electrode coatings is provided, by utilizing a combination of nano-scale self assembly and microfabrication technology. Moreover, the utility of the nanoporous electrode array in recording unit and burst activity from hippocampal slice cultures has been demonstrated.

EXAMPLE II

To help establish the efficacy of various drug or pharmaceutical coatings on a nanoporous metal material, we developed an immunostaining protocol to visualize astrocytes, microglia, and cell proliferation, which are key indicators of a foreign body response. By administering such a protocol to test tissue samples, the integrity of a tissue sample can be quantitatively assessed.

In order to test the effect of a classical anti-inflammatory drug, dexamethasone, in gliosis, we dissected 350 µm-thick hippocampus slices from postnatal day 7 Sprague-Dawley rat pups. Organotypic slices have been shown to provide a physiologically and pharmacologically relevant model, as they preserve the cytoarchitecture of the brain and provide a means to identify pharmaceuticals for in vivo validation. In addition, the tissue damage due to slice preparation partially mimics the damage induced by neural probe insertion.

The slices were seeded in a serum-containing medium (1:1:2 horse serum, Hanks' Balanced Salt Solution, and Basal Medium Eagle, supplemented with 1 mM glutamine and 30 µg/ml gentamicin). After 24 hours, the medium was replenished with a serum-free medium (Neurobasal A/B27, with 0.5 mM glutamine and 30 µg/ml gentamicin) with 1 µM dexamethasone for one week. The culture medium containing the drugs was replenished every three days.

In order to assess the proliferation of cells, BrdU (10 µM final concentration) was incorporated in each medium change. The slices were then fixed with 4% paraformaldehyde in ACSF for two hours and subsequently immunostained. We used fluorophore conjugated primary antibodies: anti-GFAP for astrocytes (red) and anti-BrdU (infra-red).

Figure 6:
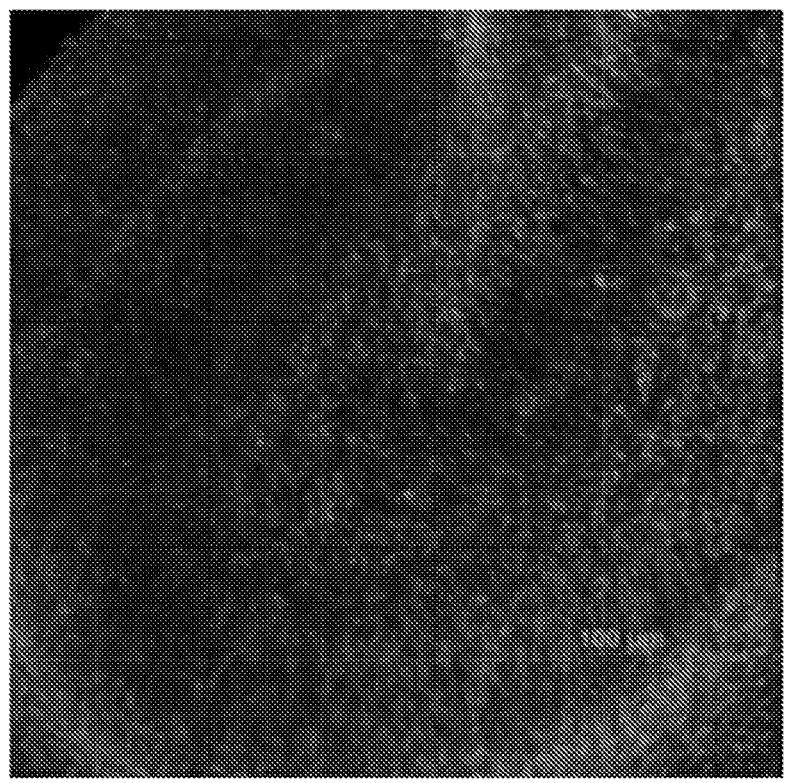
FIG. 6 shows an immunostained dentate gyrus on a hippocampus slice. GFAP is denoted by the lighter (red) color whereas BrdU is denoted by the darker (blue) color.

We imaged CA3 and DG regions of the slices using a fluorescent confocal microscope at 7× magnification. FIG. 6 shows dentate gryrus (DG) region of a control slice with no drug treatment. The images were analyzed using ImageJ to determine the number of microglia (CD11b positive) and proliferating cells (BrdU positive). Dexamethasone treated slices exhibited statistically significant reduction in the number of proliferation cells (p<0.05). This data demonstrates an effective protocol to quantify gliosis by immunohistochemisty.

EXAMPLE III

Having established a protocol for the evaluation of glial scarring as described in Example II, in separate trials we used fluorophore-conjugated primary antibodies: anti-glial fibrillary acidic protein (anti-GFAP) for astrocytes (red) and anti-BrdU (infra-red), and subsequently imaged CA3 and DG regions of the slices using a fluorescent confocal microscope at 7× magnification and clearly identified BrdU and GFAP positive cells. For live microglia staining, we applied fluorophore-conjugated Isolectin-B4 with the regular medium for 1 hour and imaged slices with a confocal microscope. For image analysis we used Fiji (ImageJ) to determine the number of proliferating cells (BrdU positive) and astrocyte reactivity (GFAP intensity).

Using the organotypic slices and immunostaining approaches, the effect of different pharmaceutical medium supplements were evaluated at various concentrations: (i) immunosuppressant rapamycin (0.1 and 1 µM), a mTOR signaling inhibitor that results in cell cycle arrest, immunosuppression, and inhibition of cell proliferation, and has neuroprotective potential; (ii) immunosuppressant FK-506 (10 and 50 µM), a calcineurin-inhibitor that has been shown to downregulate pro-inflammatory cytokine production by glial cells; (iii) anti-inflammatory dexamethasone (1 µM), an anti-inflammatory glucocorticoid steroid which has been shown to suppress astrocyte and microglia reactivity; and (iv) anti-mitotic cocktail FUA (30 µL/mL), consisting of 3 mg cytosine-β-D-arabino-furanoside (Ara-C), 3 mg uridine, and 3 mg 5-Fluoro-2-deoxyuridine).

Figure 7:
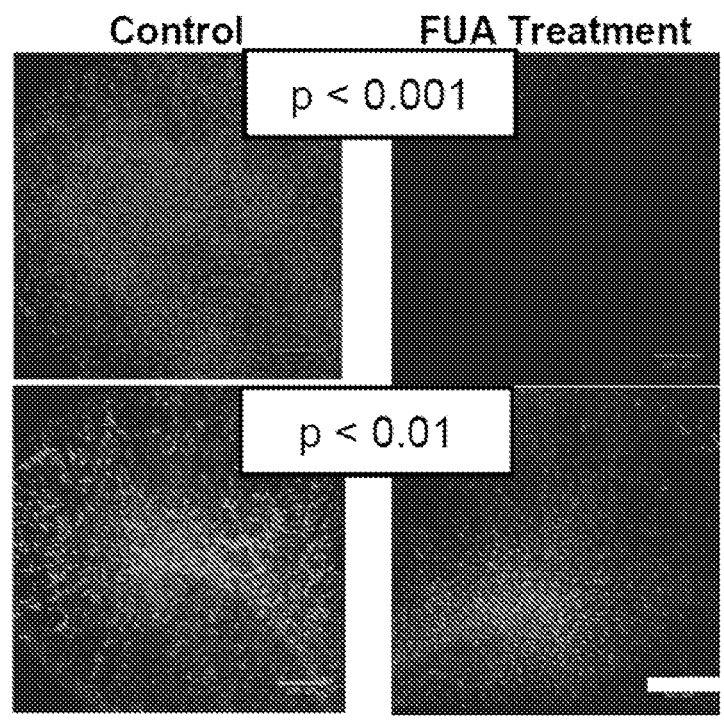
FIG. 7 illustrates that FUA treatment markedly decreases cell proliferation (blue anti-BrdU, top) and astrocytic activation (anti-GFAP, bottom) in the CA3 region of organotypic hippocampus slices (Scale bar=200 μm, all images).

The end-point fluorescent immunohistochemical quantification of gliosis revealed that, compared to untreated organotypic slices, FUA-treated slices exhibited reduced cell proliferation (p<0.001) and astrocytic activation (p<0.01) as depicted in FIG. 7, while the other pharmaceuticals exhibited no statistically significant effect. An active ingredient of FUA, Ara-C, is incorporated into the DNA of glial cells, and stops glial proliferation by disrupting DNA synthesis.

This data indicates that we have developed the capabilities for quantitative immunohistochemistry to assess the extent of gliosis, and that FUA is a good candidate for suppressing gliosis in vivo. It should be appreciated, however, that other drugs may also potentially be gliosis inhibiting such as, for example, cyclosporine.

EXAMPLE IV

As a starting point for administration, we set about establishing that nanoporous gold films or electrodes could retain and release molecules for the directed application of agents to inhibit glial scarring or electrode separation from neural tissue.

We demonstrated the potential of np-Au film in delivering pharmaceuticals by using fluorescein as a model molecule. 3 mm×4 mm~300 μm-thick np-Au films patterned on silicon chips were immersed in a 10 mM fluorescein solution in deionized (DI) water overnight. The chips were then thoroughly rinsed and placed in microcentrifuge tubes with 250 μL DI water.

The immersion solution was sampled to spectroscopically determine eluted fluorescein amount over time. The change in fluorescein concentration in the tube with respect to time was determined by collecting microliter samples at specific time points and measuring fluorescein concentration with a fluorospectrometer.

Figure 8:
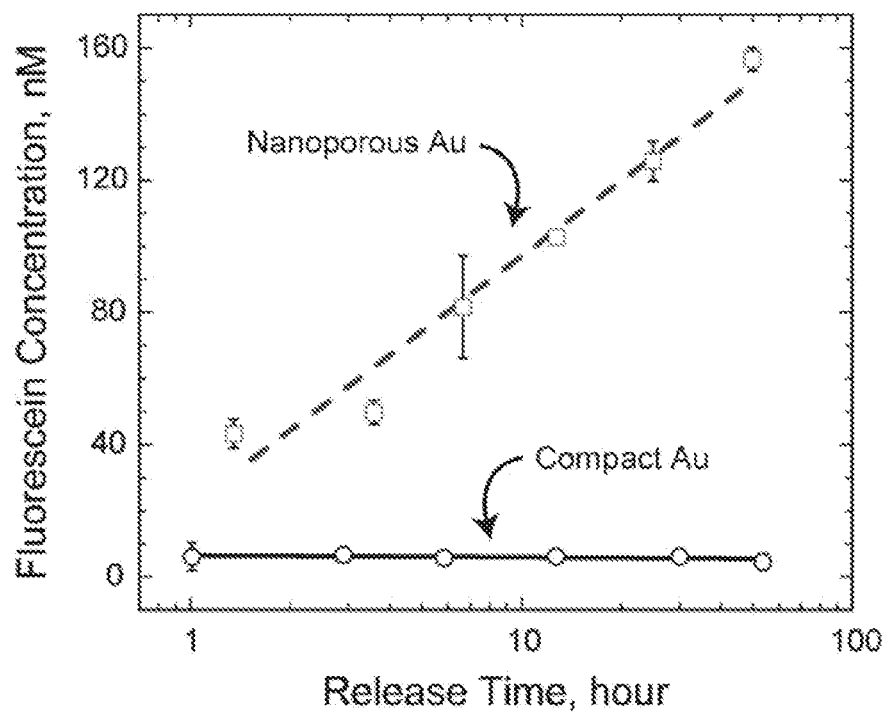
FIG. 8 provides an example in which a fluorescein concentration in a microenvironment increases over time due to the release of fluorescein molecules from np-Au films, but not from compact (i.e., substantially non-porous) Au films.

With reference to FIG. 8, the change in fluoroscein is illustrated for compact gold films and np-Au films over time. It is observed that compact gold films did not retain, and hence did not release, significant amounts of fluorescein. However, np-Au films clearly released fluorescein over the course of time.

This data supports the use of np-Au as a drug-delivery material.

EXAMPLE IV

The drug release profile may be optimized to achieve effective pharmaceutical doses in preventing gliosis by tuning the properties of the nanoporous material. Drug release from a porous material is a function of the molecule properties (e.g., hydrodynamic radius, charge) as well as the material properties (e.g., pore size, tortuosity, surface chemistry).

To optimize the release kinetics of FUA in a np-Au material, for example, the following experimentation is performed. np-Au films are fabricated on silicon chips using the aforementioned device configuration and dimensions. These fabricated chips are soaked in solutions of various FUA at different concentrations (1-1000 μL/mL) in a neurophysiologically-relevant medium of artificial cerebrospinal fluid (ACSF) for at least overnight, rinsed in ACSF, and immersed in micro-centrifuge tube (~250 μL) with ACSF. Micro-volume samples (2 μL) are collected at specific time points (i.e., 1, 2, 4, 8, etc. hours) for quantification with NanoDrop spectrometer or high performance liquid chromatography.

To alter the release kinetics, the pore size, morphology, and thickness of np-Au coatings may be modified with thermal treatment as described in Example I. In one form, these variables can be adjusted to target a sustained pharmaceutical release for at least two weeks resulting in a final concentration of 30 μL/mL FUA in 100 μL ACSF in a spherical tissue diameter of approximately 500 μm.

By performing these steps, the optimal coating properties and pharmaceutical concentration that produce the effective FUA dose or release of interest is determined or mapped. This kinetics data may be used to predict the drug release profile for nanoporous electrode with different footprints, which may be particularly helpful when np-Au is used as a controlled-drug-release platform for various medical conditions as will be described in more detail below.

EXAMPLE V

In one form, the performance of drug-eluting np-Au electrodes is evaluated in vivo and the brain tissue response to the drug-eluting implant may be quantified by immunohistochemistry. According to this form, miniaturized electrodes (i.e., drug-loaded and control) are implanted in rat brains and immunostaining is utilized to evaluate the tissue response to electrodes and cell functionality.

The miniature electrodes are fabricated on thin silicon wafers that are diced into miniature shanks (e.g., 1 mm-wide, 5 mm-long, 50 μm-thick or 2 mm-wide, 3 mm-long, 250 μm-thick). Prior to dicing, each wafer is coated with np-Au layer with the specifications that produced the desired drug release profile as established according to Example IV or another method of establishing the drug release profile (e.g., calculation). The shanks are sterilized in ethanol, rinsed in sterile DI water, and soaked in DI water until implantation.

The implants may be performed, for example, on 150-200 gram male Sprague-Dawley rats (Charles River). The rats are anesthetized and a 1.5 mm-diameter craniotomy (2 mm posterior to bregma and 4 mm from midline) is performed. Two implants per rat (one drug-loaded electrode and one plain electrode) are inserted into the cerebral cortex (depth of 2 mm from cortex surface).

Once the incisions are closed with Ethilon suture, rats are kept in their cages with bi-daily administration of analgesic Buprenex (0.1 mg/kg) for two days. At the 1-, 3-, and 6-week time-points (spanning various phases of tissue response to implants), the rats are anesthetized and perfused with 4% paraformaldehyde in PBS. The brains are dissected, postfixed overnight at 4° C., transferred to 30% sucrose in PBS, and finally sectioned with a vibratome (50 μm-thick slices in horizontal plane to a depth of 3 mm). The sections (which may be, for example, n=5 rats, 10 slices per animal) are stained with anti-GFAP, Isolectin-B4, and anti-BrdU to quantify gliosis, by expanding the immunohistochemistry and statistical image analysis described earlier. A paired t-test ($p<0.05$) is used to compare GFAP intensity and number of isolectin-B4 and anti-BrdU positive cells within a 1 mm-diameter circle around the electrode trace.

According to this method, the amount of reduction of gliosis achieved with a particular drug coating may be observed.

EXAMPLE VI

In order to assess the toxicity of np-Au, we cultured organotypic hippocampus slices on an array of np-Au patterns (30 μm-diameter, 200 μm spacing) on glass cover slips, which mimic the surface of the device. The slice was dissected and cultured as described earlier. On day-in-vitro (DIV) 12, the slice was fixed and stained with SYTO 10, which leads to a Nissl-like staining of healthy neurons.

Figure 9:
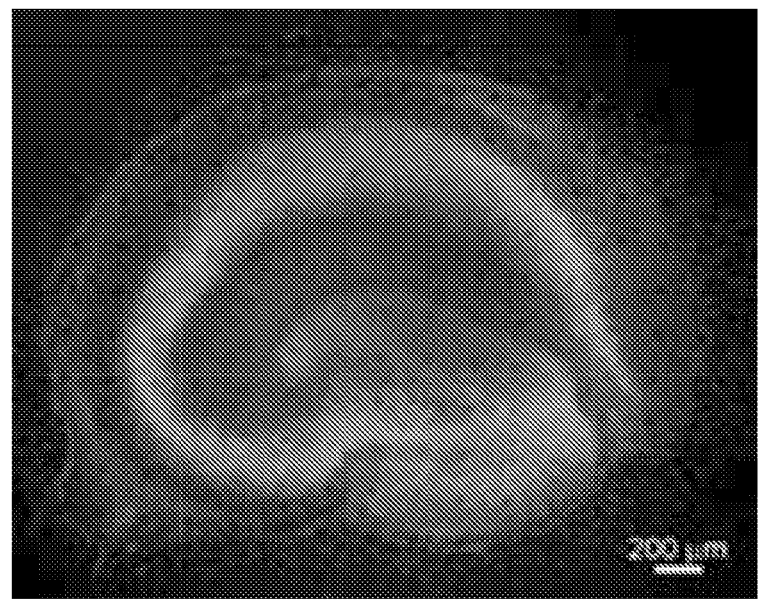
FIG. 9 is a 2-channel bright-field and fluorescent composite image that shows well-defined neuronal layers (SYTO 10-staining) which suggest that np-Au does not affect neuronal health. Micro np-Au spots are visible on the background.

FIG. 9 demonstrates that the neuronal layers in the hippocampus (CA1 and CA3 pyramidal layers, and granule cell layer) maintain their typical healthy morphology when cultured on a np-Au coating.

EXAMPLE VII

While immunosuppressant drugs are effective in alleviating glial activation, doses may be identified that do not go so far as to impair normal neural function. Activated astrocytes play a role in gliosis by encapsulating the implanted electrodes and hindering their recording sensitivity. At the same time, astrocytes express membrane transporters for sequestering several neurotransmitters such as glutamate and GABA to sustain the proper function of neurons. In addition, aquaporin membrane proteins play a role in water homeostasis.

Following the implantation of drug-eluting electrodes, the brain may be stained for several cell function indicators, such as glutamate transporter protein (GLT-1) and aquaporin-4 (AQP-4), to quantify proper cell function as well as SYTO-10 (or NeuN) to visualize neuronal density. The same protocol described before (i.e., immunohistochemistry, image analysis, and statistical analysis) may be used to quantify the cell functionality.

In addition, before the formaldehyde-fixing step, the dead cells may be stained using ethidium homodimer and cell nuclei with DAPI. The ratio (number of dead cells to number of total cells) may be compared (using paired t-test, $p<0.05$) between rats implanted with a drug-eluting electrode or with a control electrode. The density of glutamate transporters and aquaporin may also be compared between the two rat groups via the image-intensity-comparison method that was used for quantifying astrocyte reactivity.

At the optimal pharmaceutical dose, the indicators of cell function (GLT-1, AQP-4, SYTO 10) will display the highest count or fluorescence, and a low dead cell ratio. This dose may be optimized further to obtain the maximum glial suppression. Accordingly, these results help to identify the optimal drug dose that both suppresses gliosis and preserves normal cell function.

EXAMPLE VIII

One problem in chronically implanted neural electrodes or chronic electrophysiology platforms is the proliferation of astrocytes over the electrode surface creates an electrically insulating layer which, in turn, reduces electrode sensitivity. In the best case, an electrode surface promotes adhesion of neurons while reducing that of astrocytes.

The data provided herein illustrates that nanoporous gold with its highly tunable morphology can reduce growth of astrocytes while not affecting the adhesion of neurons. This attribute complements np-Au's drug-delivery-mediated reduction of astrocyte proliferation.

Figure 10:
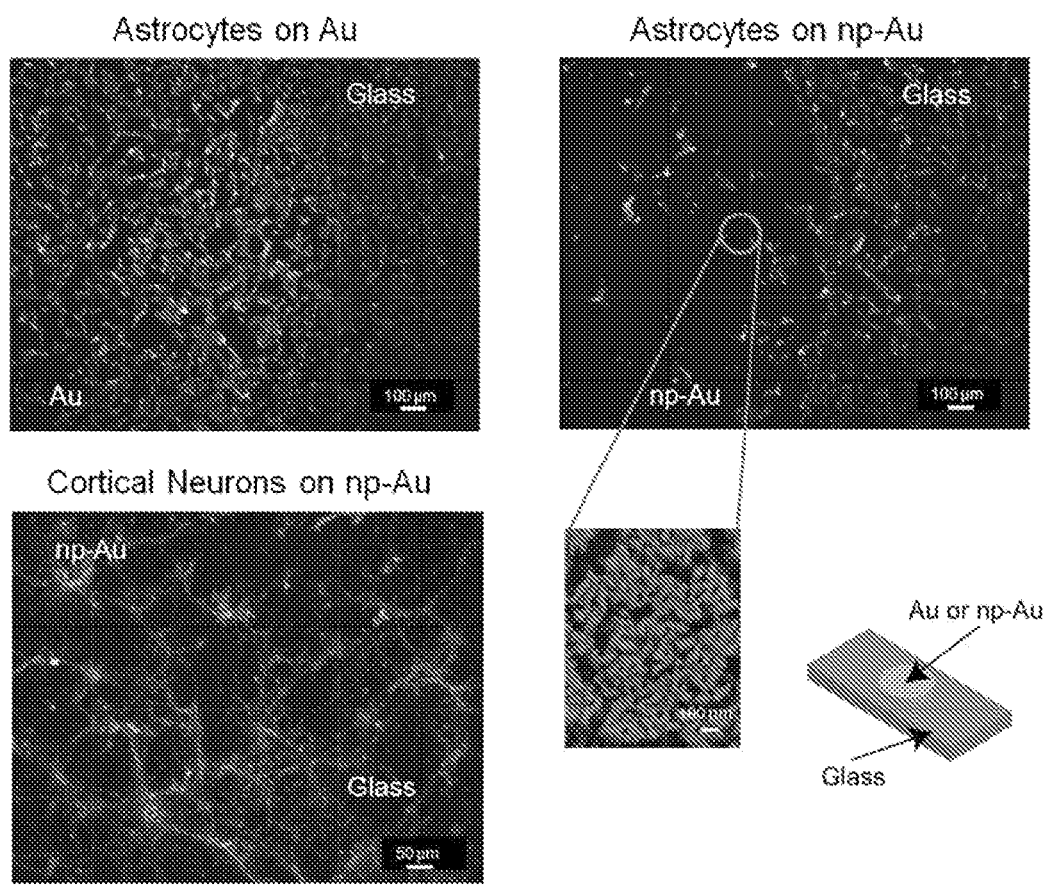
FIG. 10 shows various epifluorescence images of rodent neurons and astrocytes on nanoporous gold and planar gold surfaces. The stains are phalloidin (green for f-actin) and DAPI (blue for nucleus). The dashed red line marks the boundary between glass and metal surface. The schematic depicts the samples, on which cells are grown.

Now with reference to FIG. 10, cortical neurons proliferate on nanoporous gold and glass surfaces, while astrocytes (cells that lead to encapsulation of electrodes) exhibit reduced adhesion to np-Au surfaces in comparison to conventional planar gold surfaces. The magnified box illustrates the typical morphology of np-Au surface.

EXAMPLE IX

A complementary approach to reduce the growth of astrocytes on a device surface is to release pharmaceuticals that prevent cell growth from the nanoporous gold (np-Au) network. In order to demonstrate this concept, we loaded nanoporous gold films patterned on glass cover slips with FUA (anti-mitotic drug cocktail) at different concentrations. After the cover slips were rinsed, astrocytes were seeded onto the cover slips.

Figure 11:
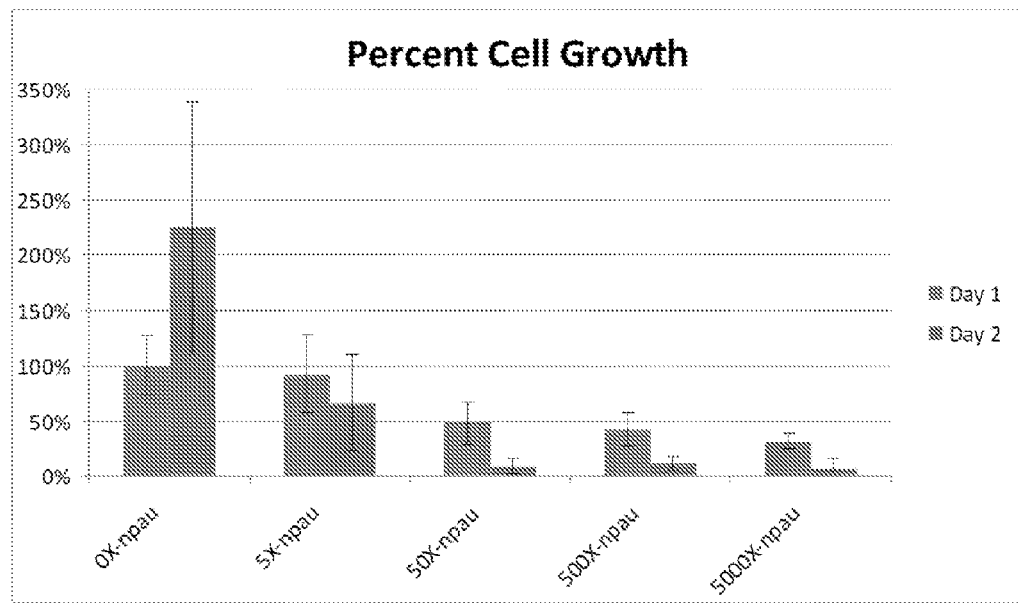
FIG. 11 shows that when astrocytes are cultured on np-Au patches that are loaded with FUA (anti-mitotic cocktail), astrocyte growth rate decreases with the concentration of the loaded drug.

Now with reference to FIG. 11, the next day (Day 1), a set of cells were imaged to quantify the number of cells adhered onto each cover slip for each drug dose. The same imaging was performed on the following day (Day 2). The number of cells on cover slips for each condition was normalized to the number of cells counted on Day 1 on the cover slip that was not loaded with the drug (i.e., Day 10×).

The results demonstrate that drug release from nanoporous films prevent cells growth in a dose-dependent manner. This approach should serve as a complementary method to the cell-specific anti-biofouling characteristics of np-Au.

EXAMPLE X

In this example, a method of fabricating an implantable np-Au patterned electrode for high-fidelity recordings is described.

Figure 12:
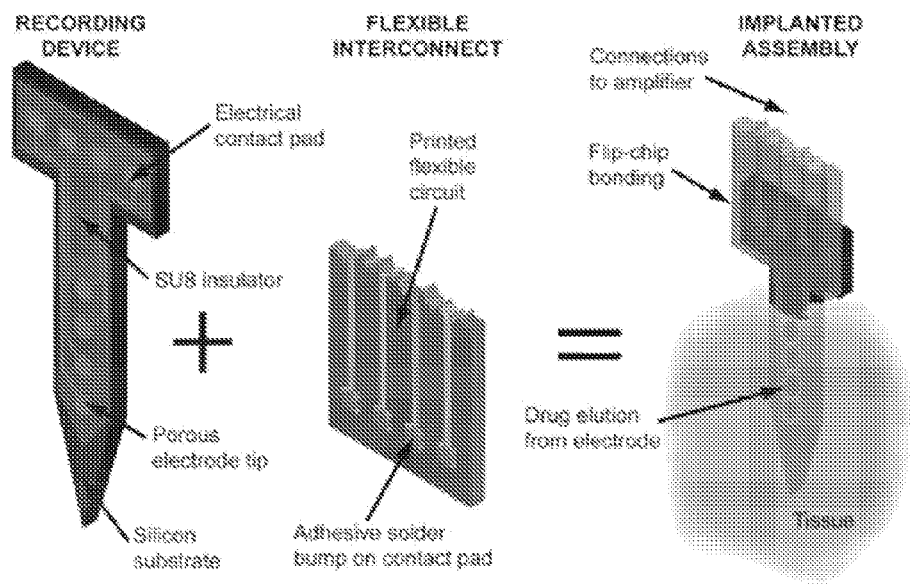
FIG. 12 illustrates a schematic of a microfabricated device for recording neural electrical activity and eluting drugs to suppress adverse tissue response.

Planar shanks with np-Au electrode patterns are fabricated to test the detection sensitivity for neural electrical activity, using microfabrication techniques to produce micron-scale np-Au patterns on silicon as illustrated in FIG. 12. Ultra-thin 50 μm-thick oxidized silicon wafers are reversibly mounted on a carrier wafer, and 300 nm-thick gold-silver (the precursor of np-Au) electrode traces are simultaneously sputter-deposited, patterned and insulated with a 5 μm-thick SU-8 photoresist to expose only the electrode tips (30 μm-diameter) and interconnects. One electrode trace serves as a reference electrode. The device shank (excluding the contact pad area) is 1 mm-wide and 5 mm-long. The entire wafer is then covered with a patterned photoresist to only expose borders of the electrode shank for through-dry etching of silicon to separate each device. The devices is immersed in nitric acid to leach the silver and produce the np-Au electrodes.

The devices are flip-chip bonded to printed flexible circuits and the assembly is secured with silicone epoxy. The assembly is interfaced to data acquisition instruments.

Electrode impedance and connectivity may be verified in ACSF using the method described before. Using the same procedure, fabricate standard gold electrodes as controls may also be fabricated. This protocol produces dozens of high-sensitivity recordings devices (sufficient for an entire course of experiments) from a single batch.

EXAMPLE XI

The fabricated electrodes are implanted into animals for acute electrophysiological measurements in vivo. The performance of np-Au electrodes is evaluated in recording neural electrical activity with high signal-to-noise ratio due to their high effective surface area.

The fabricated electrode is sterilized in ethanol and implanted using the procedure described earlier for gliosis studies with slight modifications based on the electrode implantation protocol used by our group and others. Once the animals (e.g., 5 rats) are anesthetized, a 2-cm mid-sagittal incision is made on the scalp to reflect the skin and expose the entire dorsal portion of the skull. After removing the periosteum, two small (approximately 1.5 mm) holes are drilled, and the dura mater is reflected to allow electrode insertion through the pia mater. Intrahippocampal electrodes are placed bilaterally (one np-Au and one Au electrode) in the granule cell layer of the dentate gyrus (2 mm posterior to bregma, 4 mm from midline, 3.3 mm-deep from cortical surface). Dentate gyrus is shown to be involved in the seizures during temporal lobe epilepsy and rodent kainate models. The holes are filled with gelfoam and the connector, as well as the wiring, is secured using dental acrylic. The skin is sewn back.

The implanted device is connected to an amplifier (EX4-400, Dagan Corporation) fitted with high-impedance pre-amplifier stage (4002, Dagan Corporation). Neural recordings are taken at six time points two hours apart by connecting the flexible interconnect from each rat to the instrumentation one at a time to record the spontaneous neural activity for 5 minutes (following signal stabilization). The signals are filtered, digitized, and channeled to computers via LabView data-acquisition card and software. The data is continuously stored on computers and written to DVDs for offline analysis.

The signal-to-noise ratio (SNR) is calculated using the electrophysiology data from the 6 different time recording windows. The average SNRs from np-Au and standard Au electrodes is compared (using paired t-test, p<0.05) to verify the sensitivity of porous electrodes in monitoring unit activity during an acute recording. The electrode locations (marked with lesions created by passing approximately 50 µA current through electrodes for 10 seconds) are examined via postmortem via cresyl violet staining of cryosections to validate the spatial accuracy of implantation.

EXAMPLE XII

Chronic recordings are performed by maintaining long-term stability of electrodes. Instability of electrodes during chronic recordings has previously proven to be a major challenge for the above-cited reasons. Here, we evaluate whether np-Au electrodes loaded with pharmaceuticals prevent electrode deterioration and maintain high-fidelity recordings.

A group of np-Au electrodes (with coating thickness and morphology that achieved the minimal tissue reaction as determined above) are loaded with the pharmaceuticals. The previous characterization of release kinetics are used to design the appropriate loading dose and coating morphology. The electrodes are implanted as described above and chronic recordings are taken for up to 1 month. The electrical connection to the flexible polyimide film is reversible; therefore the animals do not need to be continuously connected to the recording apparatus. Instead, the electrical connection is established for 12 hours at a time, 3 times every week for 1 month.

As a complementary verification of electrode viability, the impedance of implanted electrodes at each time point may be measured, using procedures developed elsewhere.

The recordings are processed and statistically analyzed, as described above, in order to compare the change in SNRs and electrode impedances over the course of one month between drug-loaded and plain np-Au electrode implants.

EXAMPLE XIII

While np-Au is able to elute drugs over a long period of time, the application of an electrical field may be used to control whether or not elution occurs. np-Au exhibits strong capillary wetting for transporting molecules in planar thin coatings, which may enable the supply of additional pharmaceuticals to the device with minimal medical intervention. It has also been demonstrated that np-Au electrodes detect epileptiform activity with high sensitivity.

The combination of these functions provides a platform that can monitor and modulate neural activity. Epileptic rat models are extremely suitable to validate the performance of this multi-functional device, which can then be customized for other disorders such as Parkinson's disease.

Figure 13:
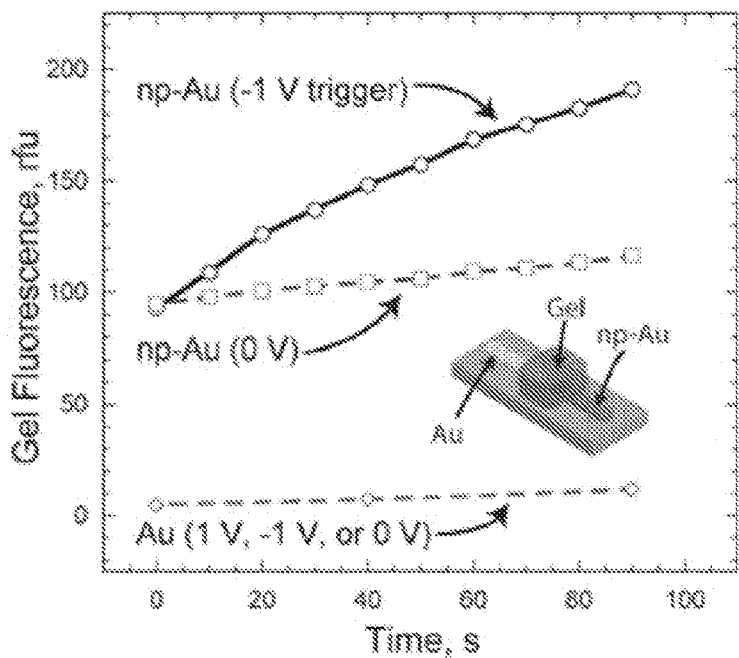
FIG. 13 illustrates that np-Au electrodes release increased amounts of fluorescein under negative voltage, while there is only passive diffusion when no voltage is applied. Compact gold electrodes do not substantially retain, and hence do not release, fluorescein at any voltage.

Now with reference to FIG. 13, it is shown that nanoporous gold can be electrically manipulated for triggered release of fluorescein, the model molecule studied above in Example IV. np-Au and compact gold were patterned as electrodes on a glass cover slip and the feasibility of electrophoretic release from micropatterned np-Au electrodes (1 mm×2 mm) was demonstrated. The electrodes are loaded with fluorescein and rinsed as described in Example IV. The molecular release is quantified by monitoring the change in fluorescence intensity within an approximately 3 mm-thick, 0.6% agarose-PBS gel placed over the electrodes. The gel has been shown to mimic diffusive and mechanical properties of brain tissue.

FIG. 13 illustrates that there is no molecular release from the compact (i.e., substantially non-porous) Au electrode (also soaked in fluorescein solution), slight passive diffusion from the untriggered np-Au electrode, and significant release from np-Au electrode at a negative voltage compared to the counter gold electrode. These data demonstrate the feasibility of using micropatterned np-Au electrodes for on-demand drug delivery.

EXAMPLE XIV

In sync with device development, substantial research efforts have focused on developing prediction and detection algorithms for epileptic seizures to precisely time the delivery of electrical stimulation. Inherently, nervous system processes are driven by both electrical and chemical signals, and therefore a significant advancement in device technology would be to modulate neural activity both electrically and chemically. A few steps have been taken toward using in situ drug delivery to treat epilepsy, but the methods employed only achieved passive release of drugs or depended on bulky external pumps for drug infusion. A limited number of studies have explored in situ drug delivery performance of microfluidic devices, again relying on external pumps thereby limiting their portability. There are other novel methods such as electrically-triggered release of molecules from polymer nanotubes.

The current limitations of in situ drug delivery include liquid storage of pharmaceuticals, dependence on external pumps to infuse drugs, and triggered release of the molecules of interest.

According to one aspect of this disclosure, a device may be fabricated or assembled that permits the triggered release of pharmaceuticals.

Complemented by the mechanism demonstrated for electrophoretic release of molecules, a device may use capillary transport through nanoporous gold to sustain the delivery of pharmaceuticals to a drug-release crevice for their triggered release. The device has the same physical dimensions as the detection device to promote easy back-to-back bonding of the two devices for simultaneous monitoring and modulating neural activity.

Figure 14:
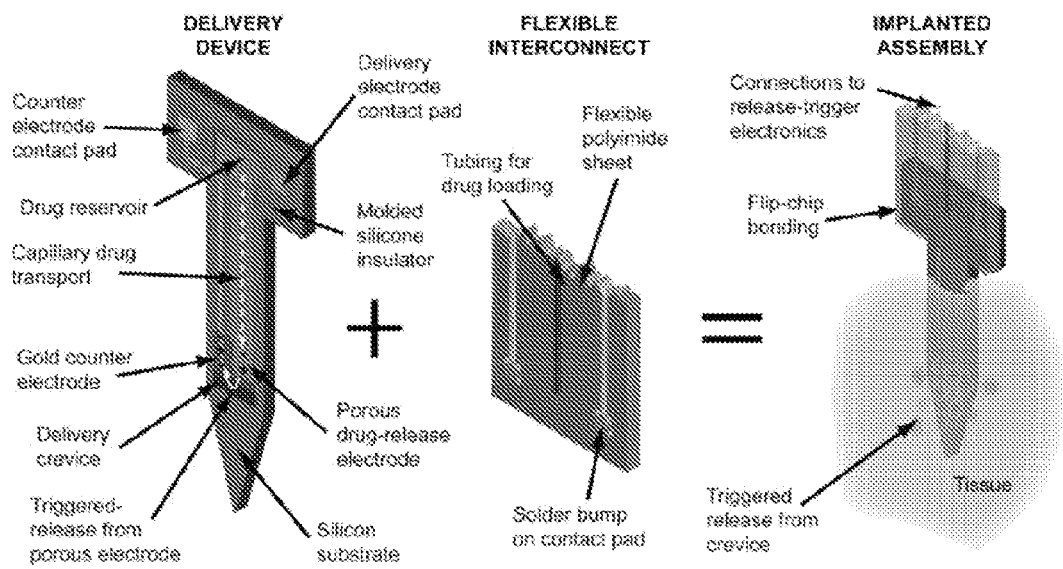
FIG. 14 is a schematic of a triggered-release device.

One challenge with electrophoretic drug delivery is limiting large electric fields within the crevice in a way that does not interfere with physiological neural activity. Accordingly, the fabricated device is composed of two electrodes (np-Au for drug delivery and planar Au as a counter electrode) extending in parallel (~100 µm inter-spacing) into the 10 µm-deep etched delivery crevice as depicted in FIG. 14. The two electrodes are covered with a thin silicone sheet. Via capillary mass transport, the np-Au electrode bridges the delivery crevice and the reservoir that contains the pharmaceutical of interest.

In order to prevent the pharmaceutical in the porous network from freely diffusing into the crevice, a small voltage (less than 1 V) is applied between the np-Au and planar Au electrodes to attract the drug molecules to the internal surface of the np-Au matrix. Upon switching the voltage between the two electrodes, the drug molecules are electrophoretically actuated, migrating out from the delivery crevice into the brain tissue.

The device operation can be validated by triggered-release into ACSF for subsequent quantification of eluted molecule concentrations as previously described. Such quantification can initially be made using sodium fluorescein, using the negatively charged fluorescein as a tracer. The drug reservoir is filled with milli-molar concentrations of fluorescein in ACSF using the tubing for drug loading, and the device is immersed in ACSF under an applied potential of 200 mV (np-Au electrode is positively charged), which has been shown to be sufficient to contain small molecules against the diffusion gradient. The voltage is then reversed to −200 mV for a duration of several hundreds of milliseconds to inject the fluorescein molecules from the np-Au matrix into the crevice, and consequently into the ACSF solution.

The efficacy of the device in containing fluorescein molecules without leakage is validated by replacing the ACSF solution while the electrode potential is set back to 200 mV in order to keep the molecules within the porous network. The solution is sampled and the fluorescein content is quantified to ascertain that no fluorescein leaked from the porous network.

Ultimately, the eluted molecule concentration is quantified spectroscopically to attain the optimal dose of nano- to micro-molar concentrations of sodium phenobarbital, which is a potent anti-convulsive drug for acutely suppressing seizures. Phenobarbital has a similar molecular weight and the same ionic charge as fluorescein. The device design and operation is perfected by varying the np-Au coating properties, drug concentration, trigger voltages, duty cycles, and drug type as necessary. In this way, a device that can be made to release charged drug molecules under precise control of applied voltage.

EXAMPLE XV

Such electrodes may be implanted to suppress systemically-induced seizure, for example, in test specimens. Once the device operation is optimized as described above, the triggered-release device is implanted into rat hippocampi as described earlier. After allowing the animals to stabilize for a week, kainate (5 mg/kg per rat) or pilocarpine (100 mg/kg per rat) in saline solution is intraperitoneally administered to promote chronic sporadic epileptic seizures in rats. Both of these agents lead to seizure development, primarily initiating in the limbic areas (e.g., hippocampus) and eventually spreading to the amygdala and cortex.

Following the initiation of a seizure (i.e., a shift in the spontaneous random electrical activity towards synchronized activity with increased signal amplitude within 1-2 hours of epileptogen administration), as detected with the implanted electrodes, the implanted electrode is triggered to release phenobarbital.

If phenobarbital does not sufficiently suppress the seizures, other common anti-convulsant drugs that are water soluble and have an ionic charge may be used. Such other pharmaceuticals include phenyloin, pentobarbital, and sodium valproate. Conveniently, these drugs all have similar molecular weights, which may mostly eliminate the need for their individual optimization.

If the intrahippocampal electrodes are not sufficient in capturing preictal activity, the recordings may be supplemented using skull screws in contact with cortex adjacent to hippocampus to acquire EEG activity. The performance may be validated by negative controls (ACSF triggered-release, n=5 rats) and positive control (intravenous injection of phenobarbital, n=5 rats). In order to increase the efficiency of detecting seizure, electrodes may also be implanted into additional neuro-anatomical locations (e.g., cortex and amyglada).

If the electrophoretic delivery is not sufficient, then microfluidic drug delivery may be employed.

Accordingly, an induced epileptic seizure may be suppressed by in situ and on demand delivery of an anti-convulsant drug from the fabricated device.

EXAMPLE XVI

A semi-closed-loop system may be constructed to detect and suppress seizures. After establishing triggered delivery of anti-convulsant drugs to suppress epileptic activity, both detection and drug-delivery electrodes may be implanted at the same time in order to achieve prototypic closed-loop control of epileptic seizures. The detection and delivery devices are bonded back-to-back using low-viscosity silicone adhesive.

The assembled device is implanted into the hippocampus as described before (a total of 5 rats are expected to be employed). Rat epilepsy models are established by administering low doses of a kainate (<1 mg/kg) or pilocarpine (<10 mg/kg) injection, as epileptic activity has been shown to be dose-dependent.

In one form, the detection electrode continuously records the electrical activity for at least a week. As neural activity is acquired, it is analyzed on a computer with minimum latency. A seizure may be identified using one or more signal processing algorithms for intrahippocampal and/or EEG recordings, including analyses of changes in signal amplitude or frequency distribution. Using these algorithms, the computer identifies whether a seizure is occurring and consequently triggers the release of anti-epileptic pharmaceuticals by applying an electrical potential across the drug-delivery electrodes. It is contemplated that any detection or prediction algorithm might be used to identify a seizure or potential seizure and nothing herein should so limit the specific detection or prediction algorithms being employed.

The amplitude of the pre-processed signal is analyzed using the existing LabView statistical tools or Matlab codes linked to LabView. The algorithm may seek high-voltage fast-activity and prominent high-voltage spiking recorded by the hippocampal electrode, which has been shown to precede a seizure. If amplitude detection is not sufficient in distinguishing epileptic and normal neural states, a frequency-domain analysis may be used, in which the intensification of distinct frequencies, such as 6-7 Hz theta waves (compared to a uniform frequency distribution) indicate an epileptic seizure.

The neural activity data and the timing of drug-release is continuously logged and reviewed offline for optimizing: (i) timing of drug-delivery; and (ii) a detection algorithm for triggering drug release.

Control experiments may be performed where there is no drug delivery to quantify the efficacy of closed-loop treatment of seizures the number of seizures that occur in rats that received drug treatment or not may be statistically analyzed.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A low-impedance nanoporous metal electrode array for measuring electrophysiological activity, the array comprising a patterned multiple electrode array including a metal alloy, the patterned multiple electrode array having a plurality of leads each extending from a contact pad to a nanoporous metal electrode tip that is configured to measure electrophysiological activity.

2. The array of claim 1, wherein the metal alloy includes gold and a sacrificial alloying element and wherein the nanoporous metal electrode tip is substantially free of the sacrificial alloying element.

3. The array of claim 2, wherein the sacrificial alloying element is silver.

4. The array of claim 2, wherein the nanoporous metal electrode tip is configured to reduce the impedance of the electrode tip relative to a substantially pore-less gold electrode tip of similar dimensions.

5. The array of claim 4, wherein the impedance of the nanoporous metal electrode tip is at least approximately twenty five times less than the impedance of the substantially pore-less electrode tip of similar dimensions.

6. The array of claim 2, wherein the electrode tips substantially comprise a nanoporous gold material and at least a portion of the leads comprises a gold alloy including gold and the sacrificial alloying element.

7. The array of claim 1, wherein the leads are substantially covered by a patterned insulation layer except for the electrode tips and the contact pads.

8. The array of claim 1, wherein the nanoporous metal multiple electrode array has a percent porosity of between approximately 26% and approximately 38%.

9. The array of claim 1, wherein the nanoporous metal multiple electrode array further supports at least one chemical agent that is configured for selective release from the nanoporous metal multiple electrode array.

10. The array of claim 9, wherein the at least one chemical agent is selected from a group consisting of anti-inflammatories and immunosuppresants.

11. The array of claim 9, wherein the nanoporous metal multiple electrode array is configured to both monitor electrophysiological activity and selectively release the at least one chemical agent to modify said electrophysiological activity.

* * * * *

UNITED STATES PATENT AND TRADEMARK OFFICE
CERTIFICATE OF CORRECTION

PATENT NO. : 9,070,492 B2  Page 1 of 1
APPLICATION NO. : 13/822747
DATED : June 30, 2015
INVENTOR(S) : Martin L. Yarmush et al.

It is certified that error appears in the above-identified patent and that said Letters Patent is hereby corrected as shown below:

In The Specification

Column 19, line 54 - "phenyloin", should be --phenytoin--

In The Claims

Column 20, line 64 - "metal electrode", should be --metal multiple electrode--

Signed and Sealed this
Twenty-fourth Day of November, 2015

Michelle K. Lee
*Director of the United States Patent and Trademark Office*